United States Patent [19]

Laubach

[11] Patent Number: 5,741,967
[45] Date of Patent: Apr. 21, 1998

[54] METHOD FOR DETERMINING OPTIMUM HORIZONTAL DRILLING DIRECTION AND DRILLING HORIZON

[75] Inventor: Stephen E. Laubach, Austin, Tex.

[73] Assignee: Gas Research Institute, Chicago, Ill.

[21] Appl. No.: 632,590

[22] Filed: Apr. 15, 1996

[51] Int. Cl.⁶ ..................................................... E21B 49/06
[52] U.S. Cl. ..................................................... 073/152.11
[58] Field of Search ........................... 73/152.11; 175/50, 175/58

[56] References Cited

U.S. PATENT DOCUMENTS

| | | | |
|---|---|---|---|
| 4,529,036 | 7/1985 | Daneshy et al. | 166/254 |
| 4,616,134 | 10/1986 | Pruett et al. | |
| 4,710,946 | 12/1987 | Hinch et al. | 73/153 X |
| 4,852,182 | 7/1989 | Herbin et al. | 73/153 X |
| 4,884,455 | 12/1989 | Vinegar et al. | 73/153 X |
| 4,929,041 | 5/1990 | Vahala et al. | |
| 5,010,253 | 4/1991 | Braglia et al. | |
| 5,036,193 | 7/1991 | Davis, Jr. et al. | 250/255 |
| 5,058,012 | 10/1991 | Hinchman et al. | 73/153 X |
| 5,105,894 | 4/1992 | Enderlin | 175/44 |
| 5,164,590 | 11/1992 | Coles et al. | |
| 5,253,719 | 10/1993 | Blauch et al. | 175/50 |
| 5,264,704 | 11/1993 | Phang et al. | |
| 5,272,916 | 12/1993 | Blauch et al. | 73/151 |
| 5,277,062 | 1/1994 | Blauch et al. | |
| 5,318,123 | 6/1994 | Venditto et al. | 166/250 |
| 5,430,291 | 7/1995 | Pepin et al. | |
| 5,482,122 | 1/1996 | Abass et al. | 175/50 |

OTHER PUBLICATIONS

Journal of Structural Geology, vol. 11, No. 5, Feb. 1989, Paleostress Directions from the Preferred Orientation of Closed Microfractures (Fluid–Inclusion Planes) in Sandstone, East Texas Basin, U.S.A., Stephen E. Laubach, pp. 603–611.

Primary Examiner—Michael Brock
Assistant Examiner—Jay L. Politzer
Attorney, Agent, or Firm—Hill, Steadman & Simpson

[57] ABSTRACT

A method for analyzing the microfractures of a sandstone formation is provided which determines an optimal horizontal drilling direction. The microfractures are analyzed with a photomultiplier-based imagining of electron-beam induced luminescence method, or scanned CL. The microfractures are categorized and a weighted average azimuth of the microfractures is generated which strongly correlates with macrofractures of the same formation. A method for classifying cementation of a sandstone formation is also provided which assists in defining an optimum drilling horizon. Suitable fracture transmissivities are provided in formations with primarily with synkinematic and prekinematic cementation.

8 Claims, 14 Drawing Sheets

△ Well location
☐ Sandstone thickness
▨ Permeability anistropy
▨ Fracture transmissivity > 50%*
▨ Fracture transmissivity ~ 50%*
▨ Fracture transmissivity < 50%*
* PST porosity index $t_{PST}$ porosity index based on percent of Pre, Syn, and Post-kinematic cement

FIG. 9A n = 63
Vector mean = 67.1

Prairie Mast 9214.6c

Class Interval = 10 degrees
Maximum Percentage = 25.3
Mean Percentage = 5.9
Standard Deviation = 5.9

Statistics
Std. Error = 11.24
R Magnitude = 0.43

FIG. 9B n = 97
Vector mean = 80.0

SFE29871.4vh traverse

Class Interval = 5 degrees
Maximum Percentage = 77.3
Mean Percentage = 25.00
Standard Deviation = 32.82

Statistics
Std. Error = 0.82
R Magnitude = 0.996

$t_{PST}$ diagrams
$t_{PST}$ porosity index

*FIG. 11A*

METHOD FOR DETERMINING OPTIMUM HORIZONTAL DRILLING DIRECTION AND DRILLING HORIZON

FIELD OF THE INVENTION

This invention relates generally to the development of existing of oil and gas fields. More specifically, this invention relates to a method of determining the optimum drilling direction based on an analysis of the microfractures found in a sandstone formation. Still more specifically, this invention relates to a method of determining the azimuth of microfractures found in a sandstone formation.

BACKGROUND OF THE INVENTION

It is becoming increasingly difficult for the oil and gas industry to find new oil and gas fields simply because there are only a limited number of possible new locations for oil and gas fields that have not already been drilled. In order to supply the world need for hydrocarbon fuels, increasing emphasis will be placed on enhancing the productivity of existing oil and gas fields. One process currently utilized is known as fracturing. In a typical fracturing process, a slurry of small beads or pellets pumped down into a well under a high pressure. The pellets then becomes embedded in the rock and create cracks or fractures which facilitate the flow of oil.

In oil and gas bearing sandstone formations, not all fractures are man-made; many sandstone formations contain natural fractures. If a well intersects with these natural fractures, the fractures will enhance the productivity of the well because fluid will flow from the formation through the fractures into the well more easily than the fluid would flow through the porous sandstone rock. While natural fractures are sometimes encountered by accident, until now, the use of natural fractures in a sandstone formation has yet to be effectively exploited as a means for increasing the productivity of a reservoir.

While it is possible to get some information about fracture strikes when large fractures fortuitously intersect a well bore, the intersection of a well bore and a fracture strike is a rare occurrence and therefore systematic mapping is not possible. Thus, there are no developed processes or methods for systematically mapping the orientation of natural fractures in a sandstone formation despite the fact that this information would vital for the efficient deployment of horizontal and directional drilling methods used in sandstone reservoirs. If it is found that the natural fractures in a sandstone formation run from east to west, the preferred horizontal drilling orientation would be from north to south so that the new well would intersect the natural fractures at a right angle. However, because there are no current processes or methods for systematically mapping natural fracture orientation, current directional drilling methods are not normally dependent upon a [study] detailed knowledge of natural fracture orientation and openness on a bed-by-bed basis.

Sandstone rock consists primarily of rock particles bound together by authigenic cement. Sandstone rock formations are frequently riddled with fractures. The fractures can increase the effective permeability of the rock if the fractures were created concurrently with or after the deposition of the cement. In other words, if the cement is "prekinematic" or "synkinematic" (i.e., the cement is deposited before or synchronous with the creation of the fractures), the fractures are less likely to be clogged with cement and the fractures are therefore more likely to be able to transmit fluid. If the sandstone grains are cemented together after the creation of the fractures, the cement is considered "postkinematic" with respect to the fractures. Postkinematic cement has the tendency to seal or block existing fractures rendering them incapable of effectively transmitting fluid. Hence, fractures that are sealed by postkinematic cement are not considered useful in terms of transmitting oil and gas. However, cement that is deposited at approximately the same time the fractures are created, i.e., synkinematic cement, or cement that is deposited before the fractures are created, i.e., prekinematic cement, do not normally have the potential for blocking fractures like postkinematic cement. Therefore, petroleum geologists and engineers are primarily interested in the fractures existing in prekinematic or synkinematic cement only.

In terms of size, fractures can be classified as either macrofractures or microfractures. Macrofractures are visible to the eye and may be larger than a centimeter in width. The spacing of macrofractures is typically on the order meters to tens of meters. Given the fact that the typical wellbore is less than twelve inches, and normally less than eight inches, the probability of encountering a macrofracture with a vertical wellbore is exceedingly small, generally only a fraction of a percent. Further, as a result, current subsurface fracture-detection methods including geophysical logging methods do not provide sufficient data to map fracture orientation with sufficient accuracy or to assure that fractures will be encountered in the specific sandstone rock layer for directional or horizontal drilling.

On the other hand, microfractures are those fractures that are visible only through sophisticated magnification techniques. In fact, microfractures are so small that their very existence is not widely known. Microfractures are more abundant than macrofractures. Microfractures are small and because they are not viewed as being the primary control of fluid flow through fractured rock, microfractures have yet been not mapped or studied. However, as shown below, the azimuths of certain microfractures correlates directly with the azimuths of neighboring macrofractures. Hence, if the azimuth of microfractures of a sandstone formation is known, that information can be used to predict the azimuth of macrofractures in the same formation, which can be used in designing a horizontal or directional drilling program.

Therefore, there is a great need in the oil and gas industry for a method of studying the direction and azimuth of microfractures and existing wells and using that information in determining the optimum horizontal drilling direction and drilling horizon in offset wells.

SUMMARY OF THE INVENTION

The present invention provides an improved method for determining the azimuth of microfractures of sandstone formation and therefore the optimum horizontal direction and drilling horizon for further development of the said sandstone formation.

The method of the present invention includes the retrieval of sidewall core samples from an existing borehole that passes through a sandstone formation. The sidewall core samples are analyzed as follows. First, a thin section is cut from the core sample that is substantially parallel to the bed angle. The thin section is then polished to microprobe standard. The polished sample is then scanned with a photomultiplier-based imaging of electronic-beam induced luminescence, commonly referred to as "scanned CL". Discrete areas of the polished sample are scanned. The scanned portions are photographed so that microfractures may be detected from the photographs. A televiewer logging device is used to determine the azimuth of the core sample. Because micro-fractures may be seen visually from the photographs of the scanned CL, the azimuth of the microfractures may also be determined.

After the cement surrounding the fractures has been determined to be primarily prekinematic or postkinematic, the microfractures are divided into four general categories. The first category (hereinafter referred to as Category I) are microfractures having lengths greater than two times the average diameter of the grains in the sandstone. Often, Category I microfractures pass through more than one grain and the cement disposed therebetween. Category II fractures have lengths about equal to the average grain diameter in the sandstone, but intersect two or more grains. Hence, Category II fractures extend between at least two grains although they are normally not long enough to pass completely through both grains. Category III fractures have lengths about equal to an average grain diameter. Further, Category III fractures cross from a grain to the adjacent cement. Category IV microfractures have lengths less than an average grain diameter and are contained entirely within a rock cement or within a grain. Microfractures not meeting any of the above criteria are disregarded. Further, microfractures that are contained within sandstone rock that is cemented with primarily postkinematic cement are also discarded as sandstone which includes primarily postkinematic cement will be excluded from the optimum drilling horizon.

Having categorized the eligible microfractures and measured their orientation on scanned CL images and having previously determined the azimuth of the samples containing microfractures using the televiewer log data, a weighted average fracture azimuth is calculated. Category I microfractures are weighted the heaviest. One preferred method applies weighing factor of 100 to the azimuths of Category I microfractures. However, the weighing factor applied to Category I microfractures may vary from 10 to 200. A smaller weighing factor is applied to the Category II microfractures, such as 10. However, a weighing factor from approximately 2 to approximately 20 may be applied to the azimuth of the Category II microfractures. Weighing factors of approximately 1 are normally applied to the azimuths of Category III and Category IV microfractures. However, it may be desirable to utilize a weighing factor of less than 1 or greater than 1 for Category III and Category IV microfractures.

Once the average microfracture azimuth is calculated, it is used to calculate the optimum horizontal drilling direction which is normally perpendicular to the microfracture strike.

It is therefore an advantage of the present invention to provide an improved method of determining the azimuth of microfractures of a sandstone formation.

Yet another advantage of the present invention is to provide an improved method of calculating a weighted average azimuth of microfractures of a sandstone formation.

It is another advantage of the present invention is to provide an improved method of determining the optimum horizontal drilling direction for a fractured sandstone formation.

Still another advantage of the present invention is to provide an improved method determining an optimum drilling horizon for a fractured sandstone formation.

Another advantage of the present invention is to provide a method for classifying authigenic cement of a fractured sandstone formation.

Yet another advantage of the present invention is to provide an improved method of classifying microfractures found in a sandstone formation.

Other advantages of the present invention will become apparent upon reading the following detailed description and appended claims, and upon reference to the accompanying figures.

BRIEF DESCRIPTION OF THE FIGURES

The invention as illustrated more or less diagrammatically and the accompanying figures wherein.

It should be understood that the drawings are not necessarily to scale and that the methods of the present invention are sometimes illustrated by graphic symbols, phantom lines, diagrammatic representations and fragmentary views. In certain instances, details which are not necessary for an understanding of the present invention or which render other details difficult to perceive may have been omitted. It should be understood, of course, that the invention is not necessarily limited to the particular methods illustrated herein.

DETAILED DESCRIPTION OF THE FIGURES

Figures 1A, 1B, 1C:
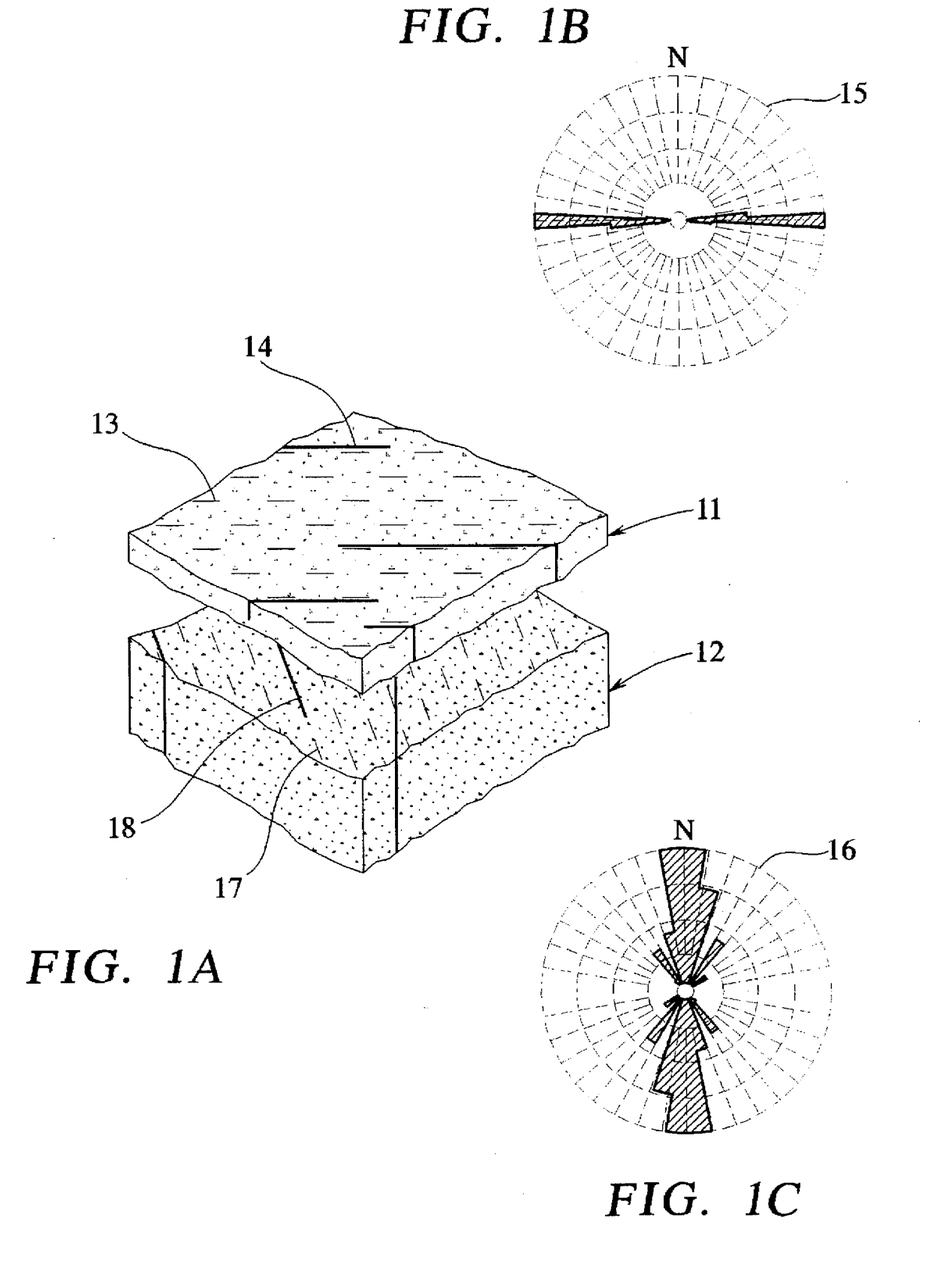
FIG. 1 is an illustration of microfractures contained in two different sandstone formations with rose diagrams indicating the microfracture strike of each formation.

FIG. 1 is an illustration of two overlying sandstone formations 11 and 12. In formation 11, microfractures are shown generally at 13 and macrofractures are shown generally at 14. A rose diagram depicting the azimuth of the microfractures 13 and macrofractures 14 is shown at 15. In contrast, the rose diagram 16 shows the azimuth of microfractures 17 and macrofractures 18 disposed in the formation 12. It will be noted that the azimuth of the microfractures 13 of sandstone formation 11 strongly correlate with the azimuth of the macrofractures 14. Similarly, the azimuth of the microfractures 17 or the formation 12 strongly correlate with the azimuth of the macrofractures 18 of the formation 12.

Figure 2:
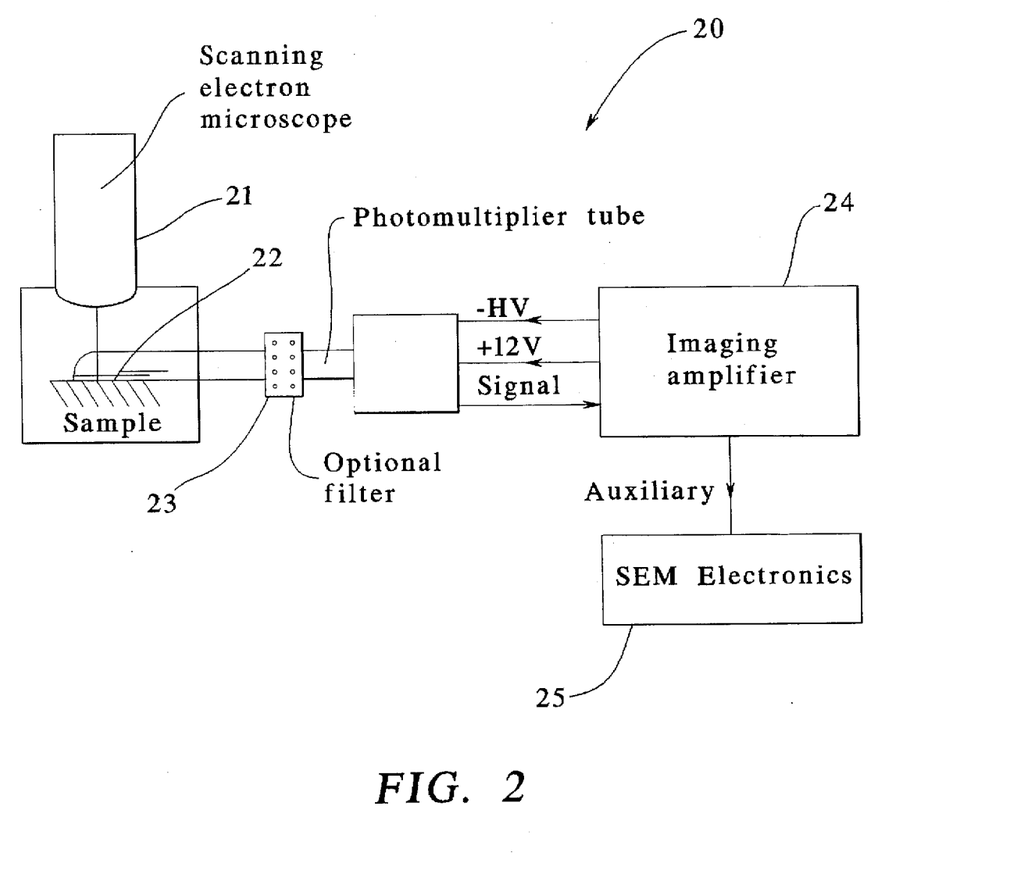
FIG. 2 is a schematic diagram illustrating equipment used for photomultiplier-based imaging of electron-beam-induced luminescence or scanned CL in accordance with the present invention.

Turning to FIG. 2, an apparatus 20 for scanning polished core samples in accordance with the present invention is illustrated. An electron microscope 21 is used to scan the sample 22. The signal is sent through a filter 23 (which is optional) before being amplified by the imaging amplifier 24. A usable image is generated by the SEM electronics 25 which can then be photographed.

Examples of photographed, scanned CL images generated by the apparatus illustrated in FIG. 2 are provided in FIGS. 3-7. The fractures shown in FIG. 3 are classified as class I fractures because they are not filled or plugged with poskinematic cement meaning that the cement shown in FIG. 3 is either primarily prekinematic or synkinematic and further because the microfractures shown in FIG. 3 have a length greater than two times the average grain diameter.

Figure 3A:
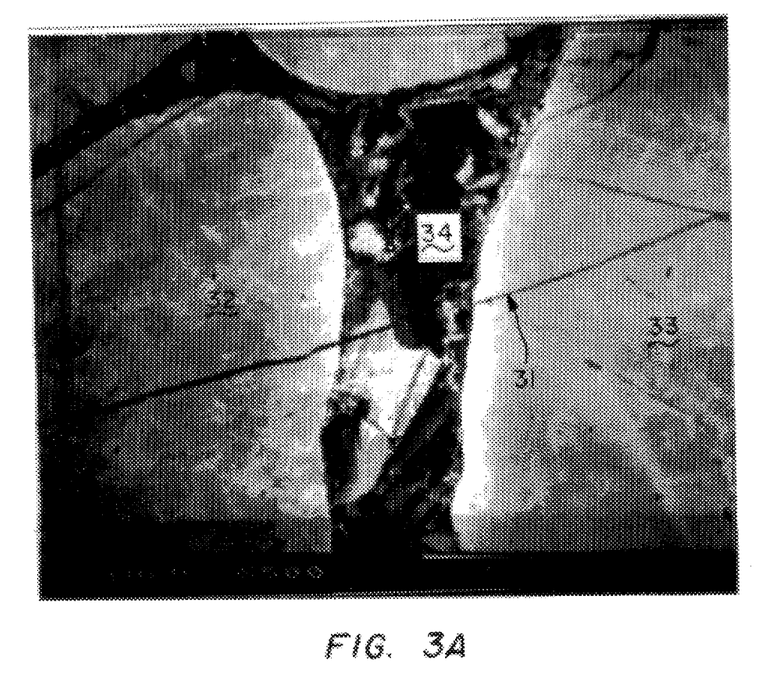
FIGS. 3a–3d are copies of photographs of Category I microfractures as taken from scanned CL images.

Referring first to the microfracture 31 shown in FIG. 3(a), it is clear that the microfracture 31 extends across the two grains 32, 33, and the cement 34 disposed therebetween. Thus, the microfracture 31 is a class I microfracture and the azimuth of the microfracture 31 is indicative of the azimuth of neighboring macrofractures (not shown).

Figure 3B:
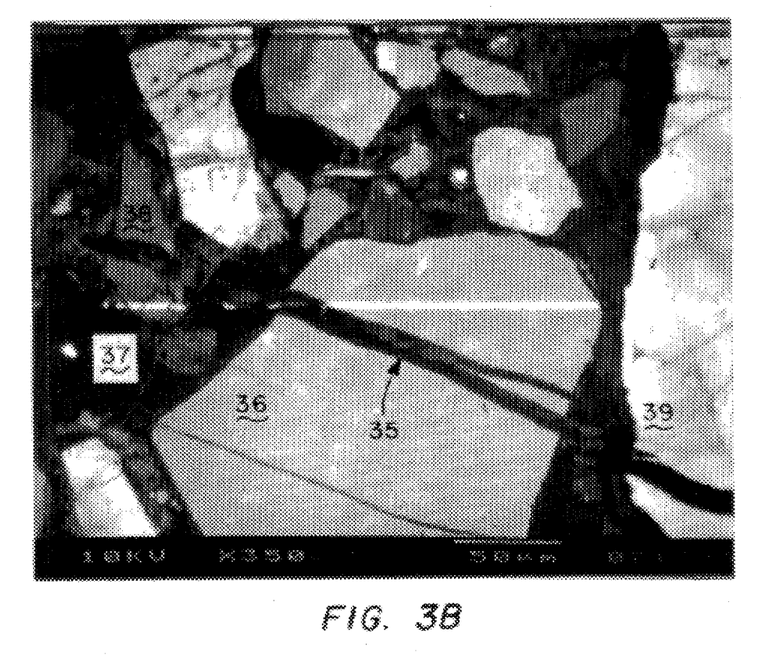

Referring now to the microfracture 35 shown in FIG. 3(b), it is clear the microfracture 35 extends across the large grain 36, through the adjoining cement 37 and through the smaller grain 38. Further, the microfracture also extends into the larger grain 39. Therefore, the microfracture 35 is also a class I microfracture.

Figure 3C:
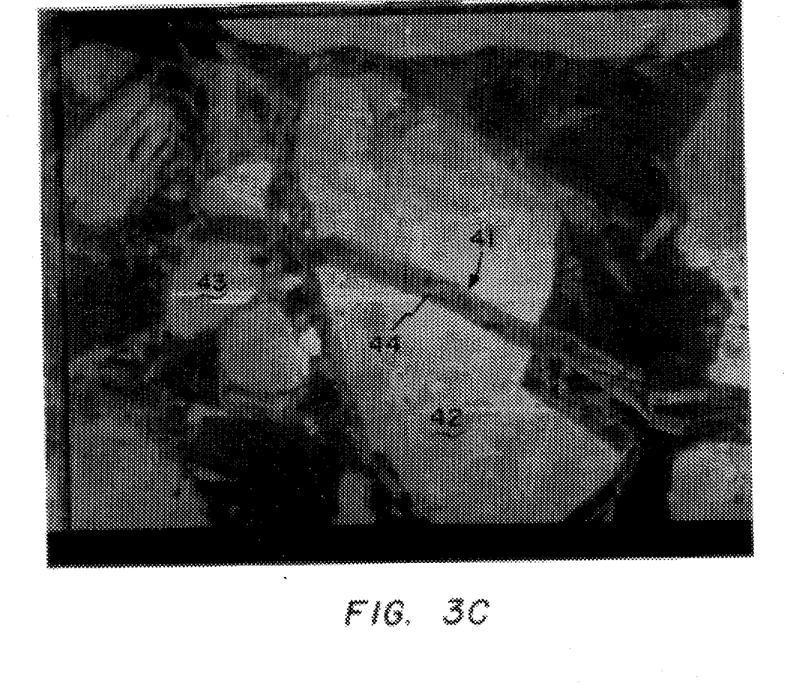

Turning to FIG. 3(c), the microfracture 41 extends through the grains 42, 43. It will be also noted that there is some fill 44 disposed within the microfracture 41. The fill 44 is attributed to synkinematic crystal growth. The microfracture 41 is also a class I microfracture.

Figure 3D:
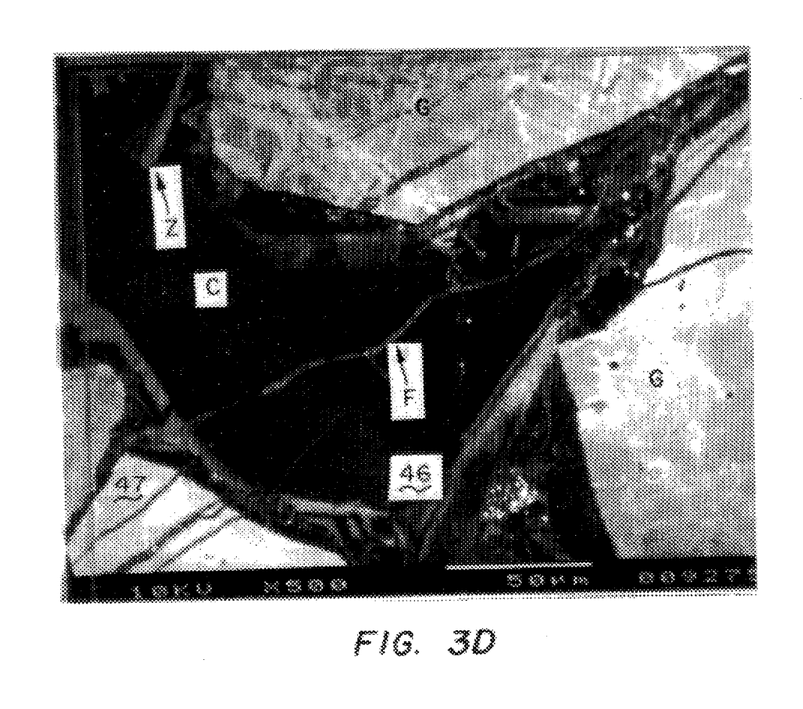

Turning now to FIG. 3(d), the fracture 45 can be seen extending through the cement 46 and into the grain 47. Because of its length, the microfracture 45 is also a class I microfracture.

Figure 4A:
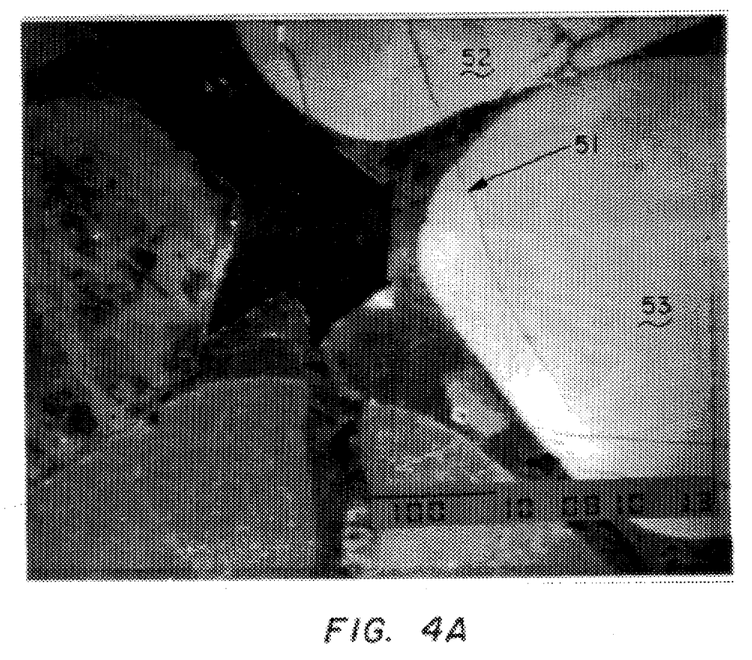
FIGS. 4a and 4b are copies of photographs of Category II microfractures taken from scanned CL images.
Figure 4B:
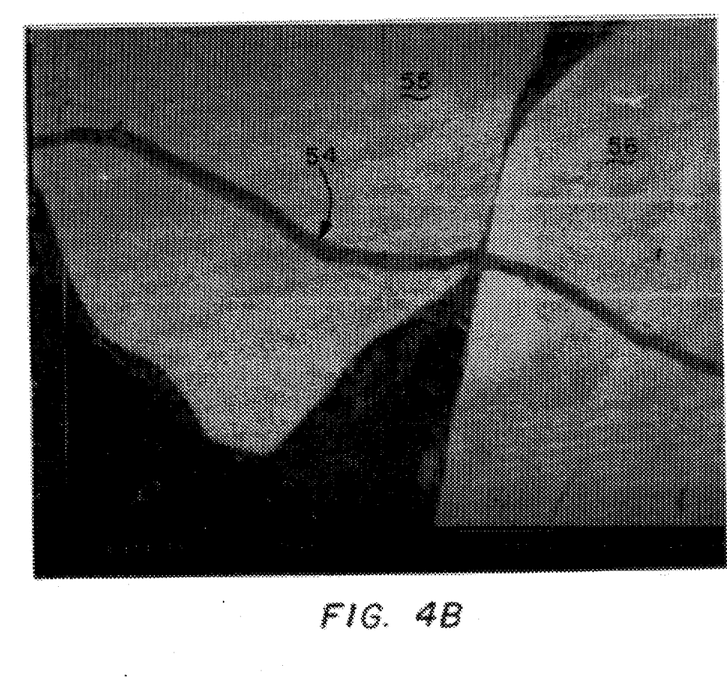

FIG. 4 includes photographs of Category II microfractures taken from scanned CL images. As shown in FIG. 4a, the fracture 51 extends from the grain 52 to the grain 53 but terminates within the grain 53. Thus, the microfracture 51 has a length close to the average grain diameter and less than two times the average grain diameter and extends between two grains 52, 53 and therefore falls into category II. Similarly, as shown in FIG. 4b, the microfracture 54 passes through grain 55 and into grain 56 before terminating within grain 56 (not shown).

Figure 5A:
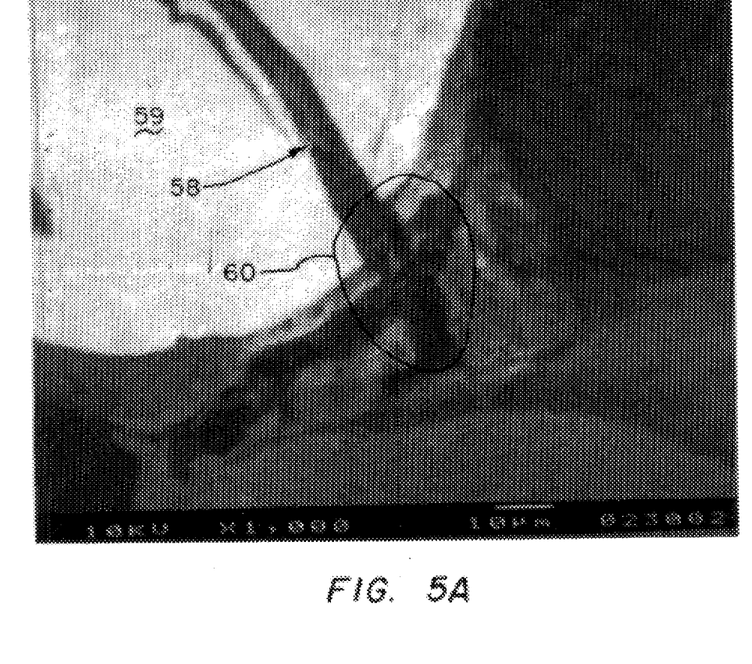
FIGS. 5a and 5b are copies of photographs of Category III microfractures taken from scanned CL images.
Figure 5B:
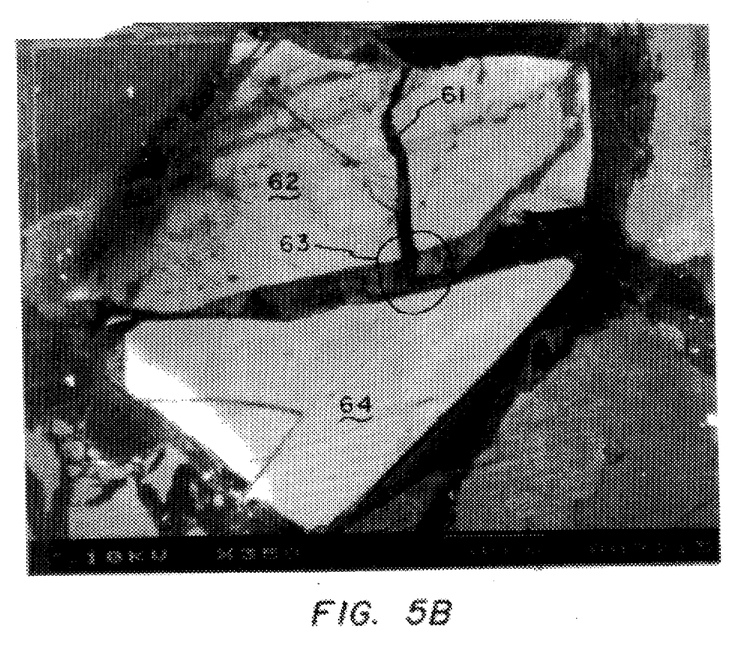

FIG. 5 include photographs of Category III microfractures taken from scanned CL images. Referring first to FIG. 5a, the microfracture 58 crosses from the grain 59 and into the cement as shown in the circle indicated at 60. Because the microfracture 59 is confined to only one grain 59 and adjoining cement, the microfracture 59 falls under category III. Similarly, referring to FIG. 5b, the microfracture 61 passes through the grain 62 and into the adjoining cement as indicated by the circle 63 but the fracture 61 does not extend into the grain 64 and therefore falls under category III.

Figure 6A:
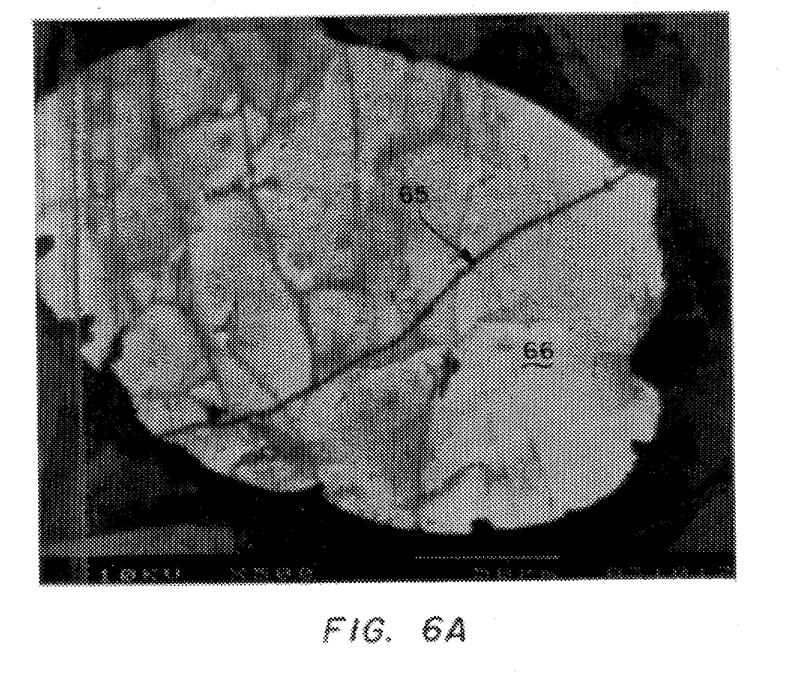
FIGS. 6a–6c are copies of photographs of Category IV microfractures taken from scanned CL images.
Figure 6B:
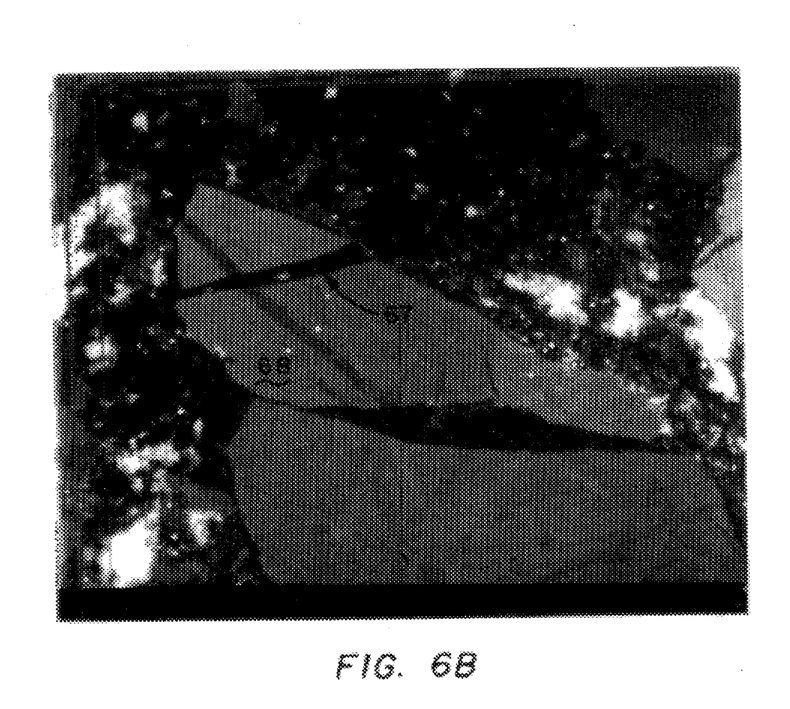
Figure 6C:
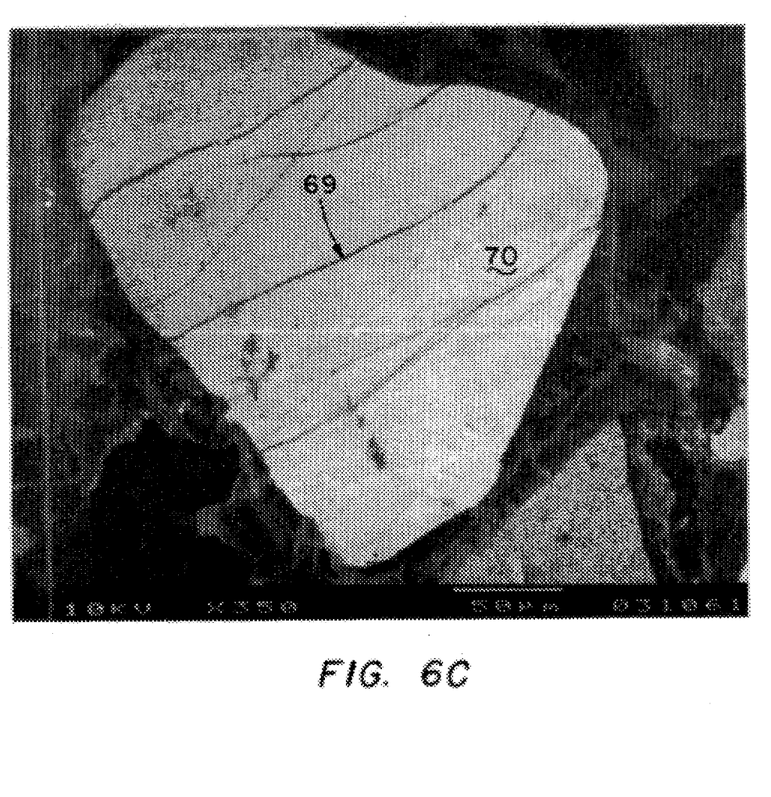
Figure 7A:
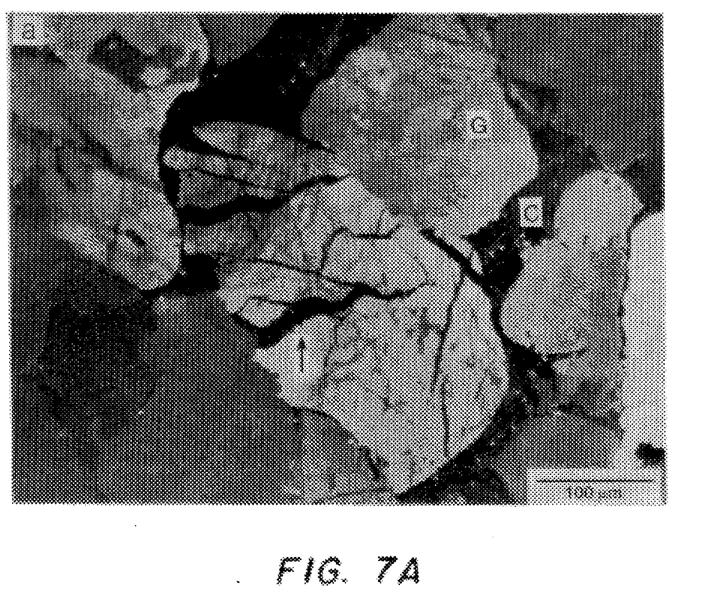
FIGS. 7a–7d are copies of photographs of scanned CL images of microfractures disposed in crisscrossing arrays and micro-fractures that were created prior to cementation.
Figure 7B:
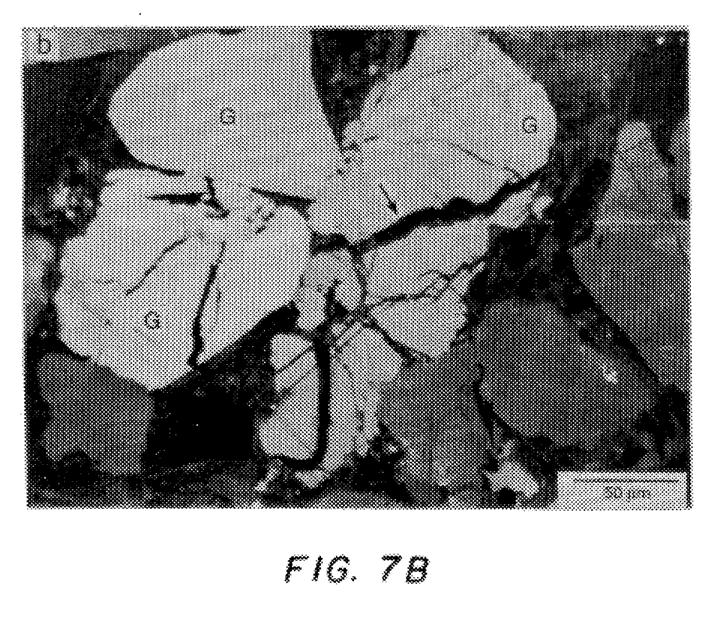
Figure 7C:
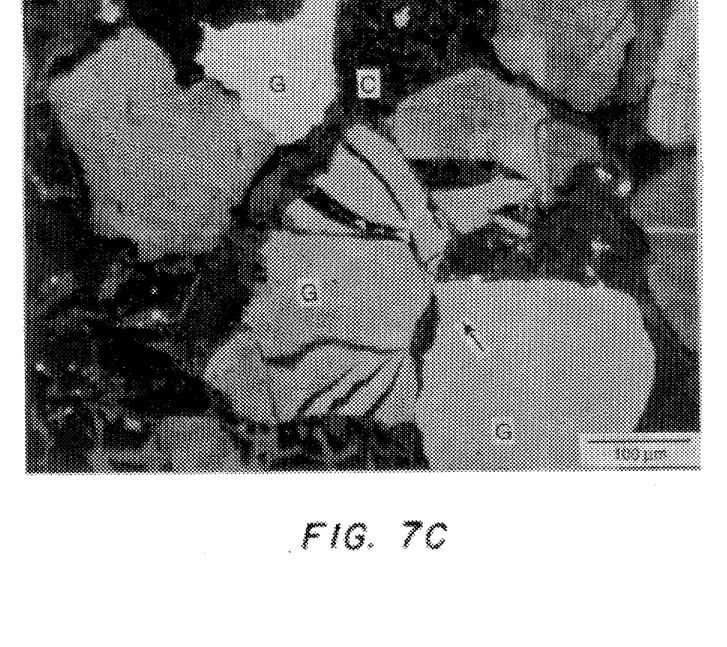
Figure 7D:
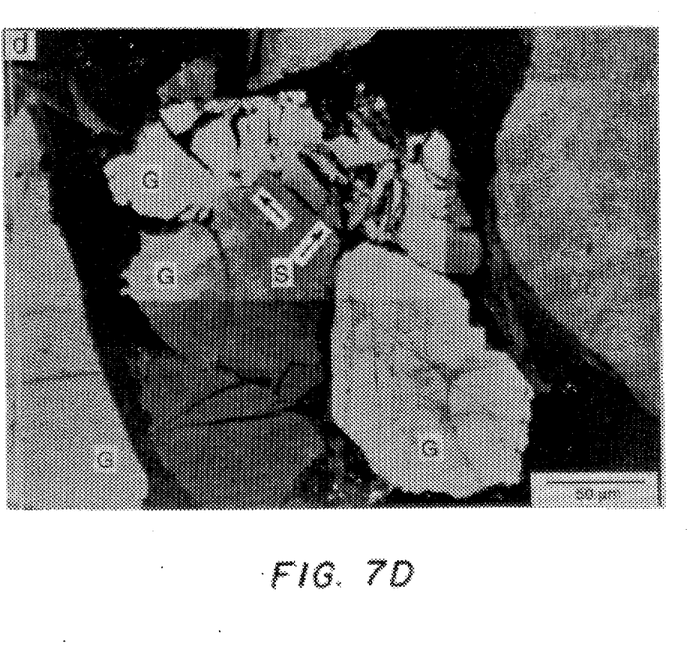

FIG. 6 include photographs of Category IV microfractures taken from scanned CL images. Referring first to FIG. 6a, the fracture 65 extends through the grain 66 only and does not pass through the adjoining cement. Similarly, in FIG. 6b, the fracture 67 extends through the grain 68 only and does not extend outward into the adjoining cement. Finally, in FIG. 6c, the fracture 69 also extends through the grain 70 only and not into the adjoining cement. Because the fractures 65, 67 and 69 extend through one grain only and not into another grain or through adjoining cement, the grains 65, 67 and 69 fall under category IV.

Referring now to FIG. 7, examples of microfractures that do not meet the criteria of Category I, II, III or IV are illustrated. Specifically, the microfractures shown in FIG. 7(a) and FIG. 7(b), are arranged in crisscrossing arrays and are apparently the result of crushed grains. In FIG. 7(c) and 7(d) the fractures appear in a radiating pattern, also apparently a result of crushed or shattered grains.

Figure 8:
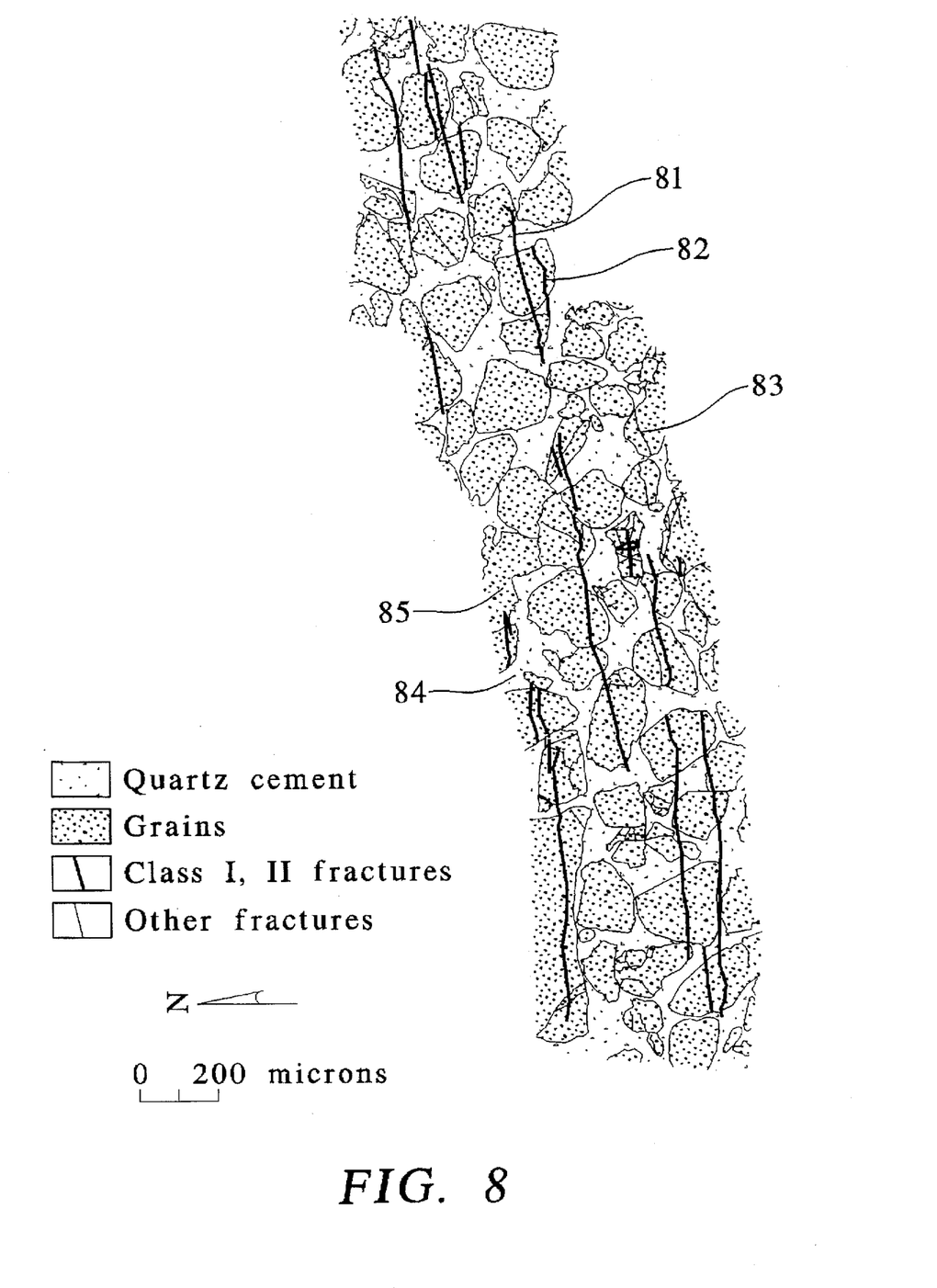
FIG. 8 is a map of microfractures revealed by scanned CL imaging.
Figure 9A:
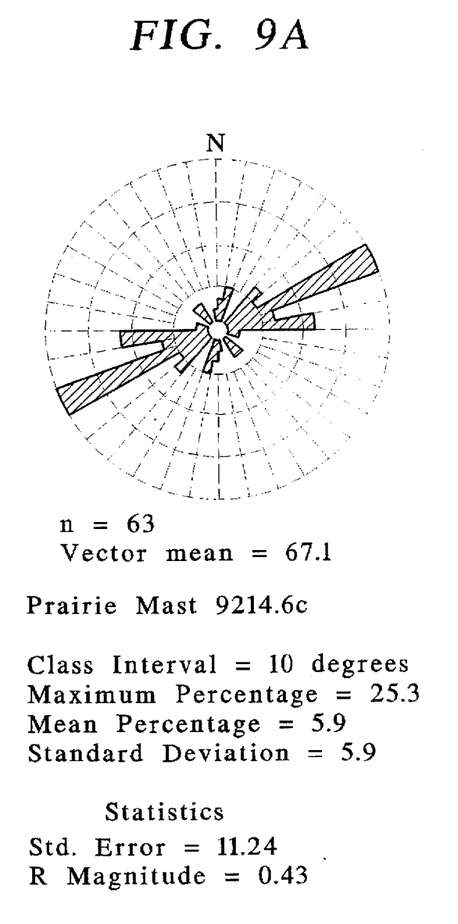
FIG. 9 is an illustration of two rose diagrams showing the microfracture strike for two gas wells in east Texas.
Figure 9B:
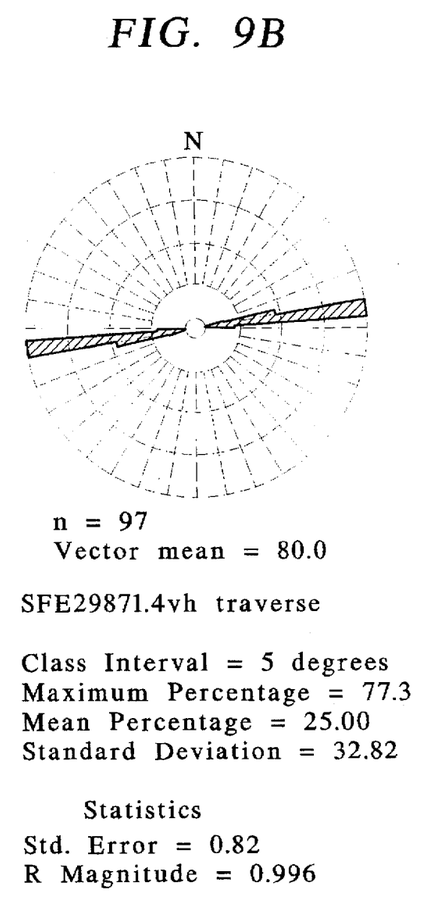

Turning to FIG. 8, a map of sealed microfracture traces revealed by scanned CL imaging is provided. Class I and class II are shown in the dark lines 81, 82 respectively. A class IV is shown at 83. The quartz cement is shown at 84 and grains are shown at 85. FIG. 9 is an illustration of rose diagrams indicating the azimuth of mapped microfractures.

Figure 10:
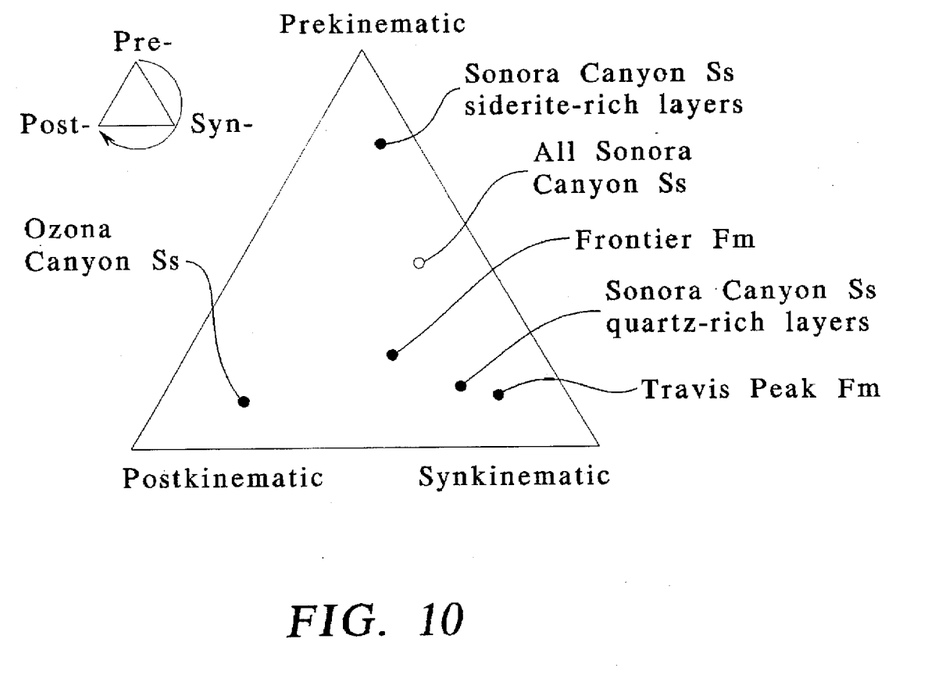
FIG. 10 is a schematic diagram illustrating the classification for authigenic cementation of formations as being prekinematic, synkinematic or postkinematic.
Figure 11A:
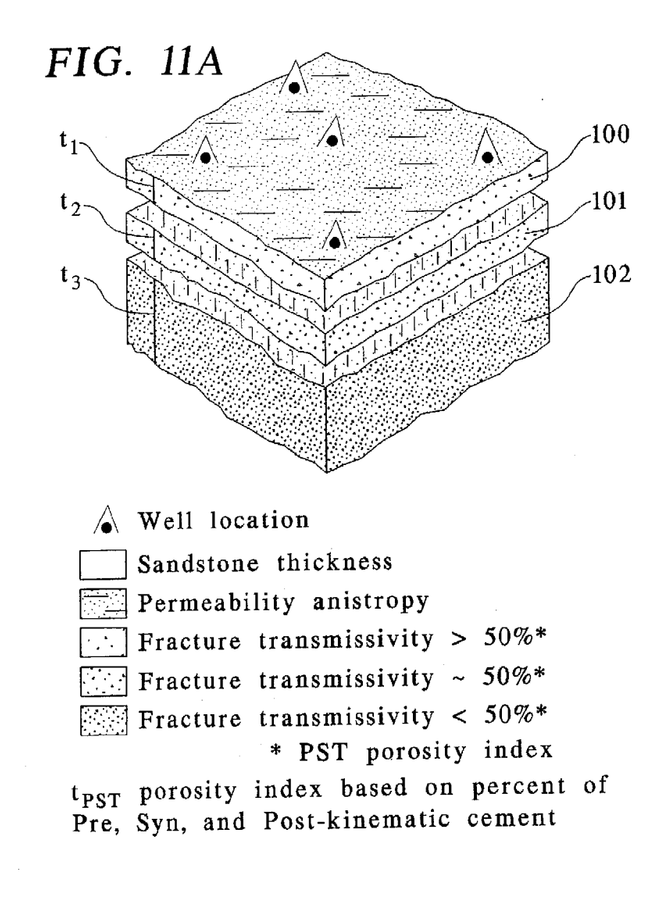
FIG. 11 is a schematic diagram of three overlying sandstone formations with varying fracture transmissivities.
Figure 11B:
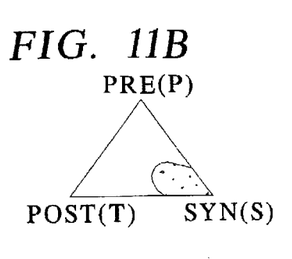
Figure 11C:
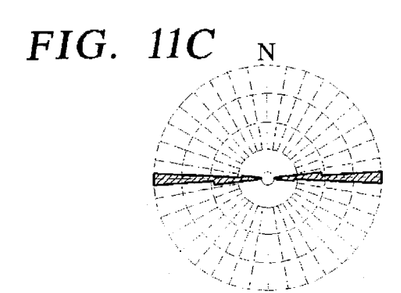
Figures 11D, 11E, 11F, 11G:
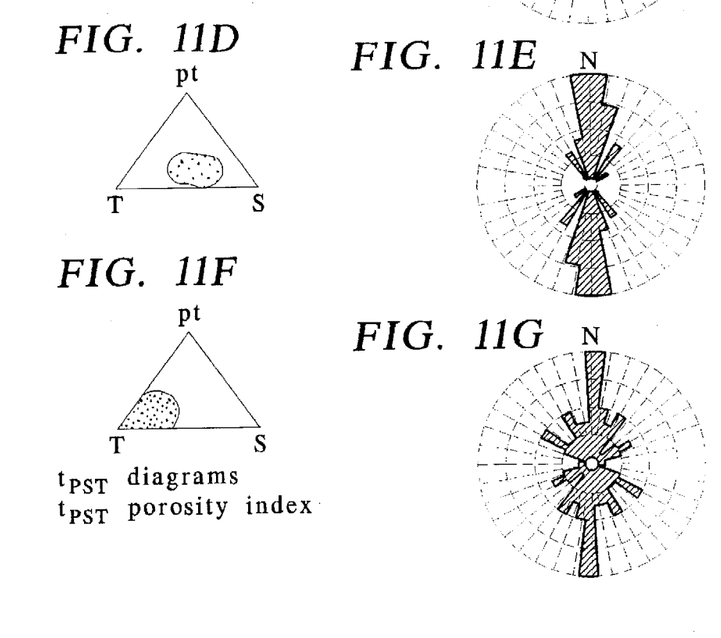

FIG. 10 is an illustration of new classification system for cement and FIG. 11 illustrates the employment of the new classification system illustrated in FIG. 10, in combination with microfracture analysis described above. Returning to FIG. 10, cement is classified as prekinematic, synkinematic or postkinematic. For purposes of the present invention, only microfractures surrounded by prekinematic and synkinematic cements are classified and used for mapping purposes. Microfractures and macrofractures that are surrounded by postkinematic cement are created prior to the deposition of the cement and are therefore plugged by the subsequent deposition of cement. The porosity contributed by microfractures and macrofractures surrounded by postkinematic cement is considered to be negligible. Beds that are dominated by synkinematic cement tend to preserve the fractures capable of transmitting fluid because the fractures are in a process of opening as the cements precipitate. In contrast, those beds with greater than 10% postkinematic cement do not effectively transmit fluid through fractures because the late cement deposition tends to block flow through the fracture networks.

Turning to FIG. 11, three overlying sandstone formations 100, 101, 102 are illustrated. The cement of formation 100 classified as being predominantly synkinematic and therefore the microfracture transmissivity is estimated to be greater than 50%. In contrast, in formation 101 the cement is classified as being both synkinematic and postkinematic and therefore the microfracture transmissivity is approximately 50%. Finally, in formation 102, the cement is classified as being primarily post-kinematic and therefore the microfracture transmissivity is less than 50%. Hence, the formation 100 is the best candidate for a horizontal directional drilling program.

A method for determining the azimuth of fractures in a sandstone formation as practiced in accordance with the present invention is as follows. After a well is drilled, a plurality of sidewall core samples is taken at selected intervals throughout the sandstone formation. The azimuth of the core samples may be determined for a televiewer logging device. A thin slice of the core sample is cut at an angle that is substantially parallel to the bed angle. The slice is then polished or analyzed with a photomultiplier-based imaging of electron-beam induced luminescence, commonly referred to as scanned CL. Photographs are then taken of the scanned images. The photographs of the scanned images, are then analyzed in two ways. First, the timing of the cementation is determined to be primarily prekinematic, synkinematic, or postkinematic. If it is determined that cementation is primarily postkinematic, analysis of the fractures is not warranted because the transmissivity of fractures surrounded by postkinematic cement is normally insufficient. If the cement is primarily prekinematic or preferably synkinematic, then analysis of the microfractures is warranted.

The microfractures are then divided into four primary categories or are disregarded if they do not meet the criteria for the four categories. Again, Category I microfractures are long microfractures having length greater than two times the average grain size. Category II have lengths microfractures length equal to about the average grain size but intersect two or more grains. Category III fractures generally have lengths that are less than the average grain size, but they cross from grains into the adjoining cement material. Category IV fractures also have lengths less than the rocks average grain size and are either entirely contained within the cement or within a grain.

The azimuth of each microfracture is determined. A weighted azimuth average is then calculated whereby a weighing factor of approximately 100 is applied to the Category I microfractures. The weighing factor applied to Category I microfractures may vary from greater than 10 to 200. A weighing factor of approximately 10 is applied to the Category II fractures. The weighing factor applied to Category II microfractures may vary from 2 to 20. Finally, a weighing factor of approximately 1 is applied to the Category III and Category IV microfractures. However, the weighing factor applied to the Category III and Category IV microfractures may vary from less than 1 to greater than 1. All microfractures that do not meet the above criteria for categories I, II, III and IV are disregarded. After the weighted average azimuth of the microfractures is determined and optimal horizontal drilling direction can be determined which is normally at about a 90° angle to the azimuth of the microfracture strike. The drilling horizon is determined primarily by the cementation analysis, whereby synkinematic and prekinematic cementation is preferred and complete domination by synkinematic cementation is the most desirable.

Although only one primary method has been illustrated and described, it will at once be apparent to the those skilled in the art that variation may be made within the spirit and scope of the invention. Accordingly, it is intended that the scope of the invention be limited solely by the scope of the hereafter appended claims and not by any specific wording in the foregoing description.

I claim:

1. A method for determining the azimuth of microfractures of a sandstone formation through which a borehole has been drilled, the method comprising the following steps:
   a. retrieving a plurality of drilled sidewall core samples from the portion of the borehole passing through the sandstone formation;
   b. determining the azimuth of each core sample;
   c. cutting each sample at an angle that is substantially parallel to bed angle to provide cut samples;
   d. polishing each cut sample to provide polished samples;
   e. detecting microfractures in each polished sample with photomultiplier-based imaging of electron beam-induced luminescence; and
   f. determining the azimuth of the microfractures in polished sample.

2. The method of claim 1,
   wherein step a includes the retrieval of cores with a rotary sidewall coring device.

3. The method of claim 1,
   wherein step b includes the use of a televiewer logging device.

4. The method of claim 1,
   wherein step c is further characterized as including cutting a thin section from the core sample at an angle that is substantially parallel to bed angle to provide thin cut samples.

5. The method of claim 1,
   wherein the core samples are polished in step d to microprobe standard.

6. A method for determining the azimuth of microfractures of a sandstone formation through which a borehole has been drilled, the method comprising the following steps:
   a. retrieving a plurality of whole drilled sidewall core samples with a rotary sidewall coring device from the portion of the borehole passing through the sandstone formation;
   b. determining the azimuth of each core sample with a televiewer logging device;
   c. cutting a thin slice of each sample at an angle that is substantially parallel to bed angle to provide cut samples;
   d. polishing each cut sample to microprobe standard to provide polished samples;
   e. scanning a plurality of discrete areas on the surface of each polished sample with photomultiplier-based imaging of electron beam-induced luminescence;
   f. photographing the scanned discrete areas of each polished sample;
   g. detecting microfractures appearing in the photograph of each polished sample;
   h. determining an average azimuth of the microfractures in polished sample.

7. A method for determining a weighted average azimuth of microfractures of a sandstone formation through which a borehole has been drilled, the method comprising the following steps:
   a. retrieving a plurality of whole sidewall core samples with a rotary sidewall coring device from the portion of the borehole passing through the sandstone formation;
   b. determining the azimuth of each core sample with a televiewer logging device;
   c. scanning a plurality of discrete areas on a surface of each sample with photomultiplier-based imaging of electron beam-induced luminescence;
   d. categorizing the cement of each sample being prekinematic, synkinematic or postkinematic or combinations thereof;
   e. disregarding all samples containing more than 50% postkinematic cement;
   f. detecting microfractures appearing in each sample;
   g. subcategorizing the microfractures in each sample as being
      i. class I whereby a class I microfracture has a length greater than two times the average grain diameter;
      ii. class II whereby a class II microfracture has a length greater than the average grain diameter but less than two times the average grain diameter and a class II microfracture intersects at least two grains;
      iii. class III whereby a class III microfracture has a length less than the average grain diameter and a class III microfracture crosses from a grain into adjacent cement;
      iv. class IV whereby a class IV microfracture has a length less than the average grain diameter and are contained either entirely within a grain or within cement disposed between grains;
      v. disregarding all microfractures not falling into categories I, II, III or IV;
   h. calculating a weighted average azimuth for all the microfractures classified in step g whereby each class I microfracture is assigned a weighing factor of about 100, each class II microfracture is assigned a weighing factor of about 10 and each class III and each class IV microfracture is assigned a weighing factor of about 1.

8. A method for determining a weighted average azimuth of microfractures of a sandstone formation through which a borehole has been drilled, the method comprising the following steps:
   a. retrieving a plurality of whole sidewall core samples with a rotary sidewall coring device from the portion of the borehole passing through the sandstone formation;
   b. determining the azimuth of each core sample;
   c. scanning a plurality of discrete areas on a surface of each sample with photomultiplier-based imaging of electron beam-induced luminescence;
   d. categorizing the cement of each sample as being primarily prekinematic, synkinematic or postkinematic;
   e. detecting microfractures appearing in each sample;
   f. for samples with primarily prekinematic and synkinematic cement, subcategorizing the microfractures in each sample as being
      i. class I whereby a class I microfracture has a length greater than two times the average grain diameter;
      ii. class II whereby a class II microfracture has a length greater than the average grain diameter and intersects at least two grains;
      iii. class III whereby a class III microfracture has a length less than the average grain diameter and a class III microfracture crosses from a grain into adjacent cement;
      iv. class IV whereby a class IV microfracture has a length less than the average grain diameter and are contained either entirely within a grain or within cement disposed between grains;
      v. disregarding all fractures not being surrounded primarily by prekinematic or synkinematic cement and falling into Categories I, II, III or IV;
   g. calculating a weighted average azimuth for all the microfractures classified in step f whereby each class I microfracture is assigned a weighing factor from about 11 to about 200, each class II microfracture is assigned a weighing factor from about 2 to about 20 and each class II and each class IV microfracture is assigned a weighing factor from about 0.1 to about 2.

* * * * *